United States Patent [19]

Demand

[11] Patent Number: 4,759,712
[45] Date of Patent: Jul. 26, 1988

[54] DEVICE FOR APPLYING CONTROLLED TEMPERATURE STIMULI TO NERVE SENSITIVE TISSUE

[75] Inventor: Erhart E. Demand, Boston, Mass.
[73] Assignee: Temptronic Corporation, Newton, Mass.
[21] Appl. No.: 920,725
[22] Filed: Oct. 17, 1986
[51] Int. Cl.[4] .............................................. A61C 3/00
[52] U.S. Cl. ........................................ 433/32; 433/80; 222/146.1
[58] Field of Search ...................... 433/32, 80, 81, 215; 128/742, 400, 68.1, 303.1, 399, 401, 776, 777; 222/146.1

[56] References Cited

U.S. PATENT DOCUMENTS

| | | | |
|---|---|---|---|
| 2,767,960 | 10/1956 | Fast | 222/146.1 |
| 2,784,879 | 3/1957 | Fischer | 222/146.1 |
| 3,618,590 | 11/1971 | Frank et al. | 433/32 |
| 3,782,366 | 1/1974 | Brown | 433/32 |
| 3,841,311 | 10/1974 | Brown | 433/32 |
| 3,948,269 | 4/1976 | Zimmer | 128/303.1 |
| 4,215,698 | 8/1980 | Nuwayser | 433/32 |
| 4,249,899 | 2/1981 | Davis | 433/80 |
| 4,308,012 | 12/1981 | Tamler et al. | 433/32 |

Primary Examiner—John J. Wilson
Attorney, Agent, or Firm—Schiller, Pandiscio & Kusmer

[57] ABSTRACT

A device for and method of determining the thermal sensitivity of teeth and other nerve sensitive tissue is disclosed. The device comprises a portable probe for emitting a stream of pressurized fluid and a temperature controller for controlling the temperature of the emitted fluid. The probe includes cooling means, preferably in the form of a vortex tube for cooling the pressurized fluid and heating means downstream of the cooling means for heating the cooled pressurized fluid. The probe is covered with a replaceable sleeve made of soft, resilient material and having soft, pliable end portion for engaging the surface of the tissue under test. A temperature sensor is disposed within the probe adjacent the end of the probe where the pressurized fluid is emitted for detecting the temperature of the emitted fluid. The temperature sensor and heating means are connected to the temperature controller. Included in the temperature controller is control circuitry for supplying power to the heating means when the temperature of the emitted fluid, as measured by the temperature sensor, is below the temperature selected on a temperature set switch mounted on the temperature controller.

26 Claims, 2 Drawing Sheets

DEVICE FOR APPLYING CONTROLLED TEMPERATURE STIMULI TO NERVE SENSITIVE TISSUE

This invention generally relates to devices for and methods of determining the thermal sensitivity of nerve sensitive tissue, and more particularly to dental probes for determining the thermal sensitivity of teeth and gums.

Systems and techniques using dental probes for determining the nerve sensitivity of teeth are well-known. These systems and techniques may be categorized by the type of stimulus or stimuli they employ. The device of U.S. Pat. No. 4,164,214, for example, applies an electrical energy stimulus. The devices described in Naylor, M. N., "A Thermo-electric Tooth Stimulator", *British Dental Journal*, Apr. 4, 1961, pp 228–230, inclusive, and U.S. Pat. Nos. 3,274,995, 3,618,590, 4,308,013 and 4,350,388 apply hot and cold stimuli; while the device of U.S. Pat. No. 4,308,012 applies hot, cold and electrical energy stimuli. The device described in Smith, B. A. and Ash, M. M., "A Study of a Desensitizing Dentifrice and Cervical Hypersensitivity", *Journal of Periodontics*, Vol. 35, pp. 222–231, 1964 describes devices for applying hot, cold and mechanical stimuli; and the devices in U.S. Pat. Nos. 3,782,366, and 3,841,311 apply hot, cold, mechanical energy and electrical energy stimuli. As shown in these patents and publications, these systems generally apply the various stimuli through a hard, generally metallic probe having a hard tip constructed and contoured to directly contact the surface of the tooth.

Several problems, however, are encountered with these illustrated prior art systems and techniques particularly where they are employed to provide hot and cold stimuli. In order to apply the hot or cold stimuli, it is necessary to bring the probe tip, typically containing a thermo-electric element, into contact with each tooth in the mouth. However, it is difficult to achieve satisfactory thermal contact between the hard probe tip and all of the various teeth in the mouth. Because teeth are of different sizes and shapes, the amount of surface area contact between each tooth and the hard probe tip will vary. This variation in contact area between the probe and the various teeth makes it difficult to measure the exact temperature of the stimulus actually applied to the tooth. Additionally, the hard tip must be pressed against the tooth with a predetermined amount of pressure to insure the application of the stimulus. However, the patient response may confuse sensitivity to the pressure applied by the probe and the actual temperature stimulus. The latter situation could cause inaccurate readings to temperature sensitivity which could affect tests, for example, relating to the hypersensitivity of teeth, to certain desensitizing dentifrices, and other experimental, diagnostic and therapeutic sensitivity measurements.

Another problem of the prior art probes utilizing the thermo-electrical components for creating the various stimuli applied teeth, is that the probe must be sanitized, typically by chemicals or autoclaving, after it is used on each patient.

Until the present invention these thermo-electric devices have been considered preferred over devices providing temperature controlled fluid jets because of the difficulties in achieving the necessary temperature ranges, e.g. approximately 0° C. to 100° C., especially at the low temperature region. See, for example, the Naylor publication, cited above.

Accordingly, a principal object of the present invention is to substantially reduce or overcome the aforementioned problems and disadvantages of the prior art systems and techniques.

Another object of the present invention is to provide a system for and method of applying hot and cold stimuli to nerve sensitive tissue.

And another principal object of the present invention is to provide a probe device for and method of applying hot and cold stimuli at predetermined temperatures to nerve sensitive tissue in a reasonably exact manner without the need of applying pressure to and thus masking the thermal sensitivity of the tissue with a mechanical stimulus.

Still another object of the present invention is to provide an improved system of the type including a probe assembly for accurately controlling the temperature of and applying an airstream to nerve sensitive tissue so that hot and cold stimuli can be applied to the tissue at various preselected temperatures within a predetermined range of temperatures.

Yet another object of the present invention is to provide a system including a relatively light-weight, easily manipulated, hand-held probe assembly having a cooling system and adapted to provide hot and cold stimuli to nerve sensitive tissue.

These and other objects are achieved by a device for use in determining thermal sensitivity of nerve sensitive tissue. The device includes a probe for selectively directing a stream of temperature controlled, pressurized fluid in the direction of the tissue. The device also includes a temperature controller adapted to be connected to a source of pressurized fluid and coupled to the probe for providing the temperature controlled, pressurized fluid to the probe. The probe includes a cooling device for cooling the pressurized fluid below or at the lower limit of a range of desired temperatures and a heating device for heating the cooled pressurized fluid to a preselected temperature within the aforementioned range.

In accordance with another aspect of the present invention, an improved method is provided of measuring the thermal sensitivity of nerve sensitive tissue at each of a plurality of test temperatures within a range of temperatures. The method comprises the steps of:

cooling a stream of fluid below or at the lower limit of the range of temperatures;

heating the cooled stream of fluid to any one of the temperatures of the plurality in response to a control signal; emitting the fluid stream from a tip of a probe;

positioning the tip relative to the surface of nerve sensitive tissue of a patient so that the stream emitted from the tip contacts the surface; and generating the control signal, wherein the latter step includes the steps of (1) setting the temperature of the stream to a selected level of one of the test temperatures, (2) measuring the temperature of the stream as it is emitted from the tip, and (3) adjusting the control signal so as to vary the heat applied to the stream until the temperature of the stream reaches the selected level.

Other objects of the invention will in part be obvious and will in part appear hereinafter. The invention accordingly comprises the processes involving the several steps and the relation and order of one or more of such steps with respect to each of the others, and the apparatus possessing the construction, combination of elements, and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings wherein.

Figure 1:
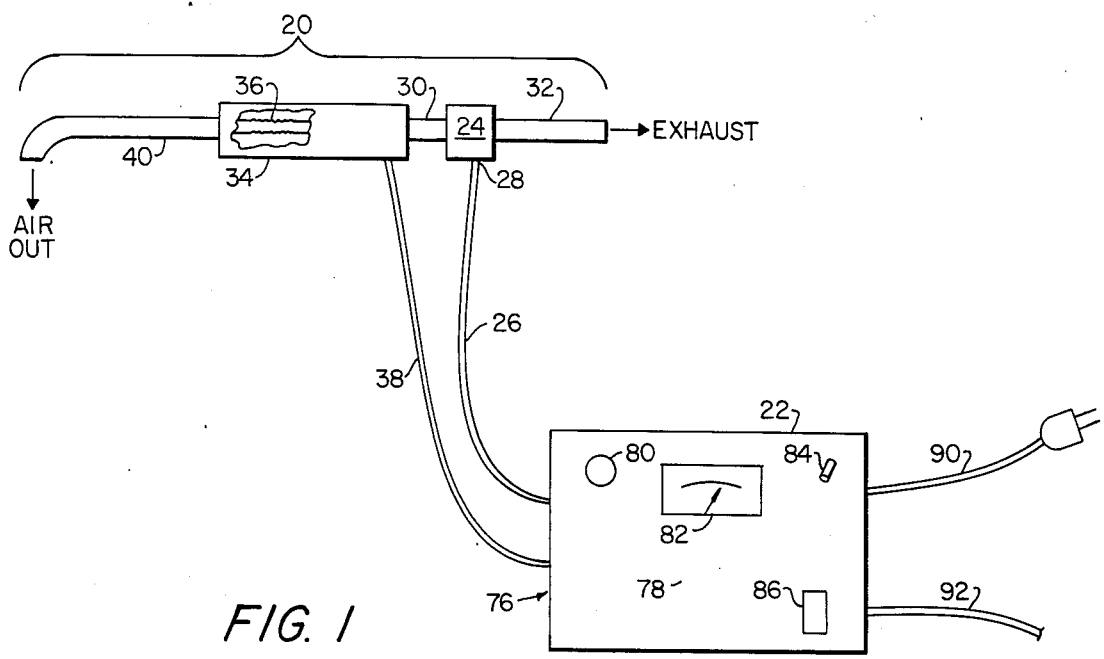
FIG. 1 is a front elevation view of the preferred embodiment of the present invention with a portion of the probe assembly broken away to reveal the heating element.

The preferred embodiment of the apparatus of the present invention, as illustrated in the drawings, generally comprises probe assembly 20 and temperature controller 22. The illustrated apparatus is particularly adapted for testing the sensitivity of teeth with hot and cold stimuli. Probe assembly 20 is provided for heating and cooling a stream of pressurized fluid in the form of compressed air, and for directing the air into contact with nerve sensitive tissue, such as a tooth or the gum. Temperature controller 22 is cooperative with the probe assembly for supplying and controlling the temperature of the pressurized air emitted from probe assembly 20. In use, temperature controller 22 is connected to sources of compressed air and electrical power.

Figure 2:
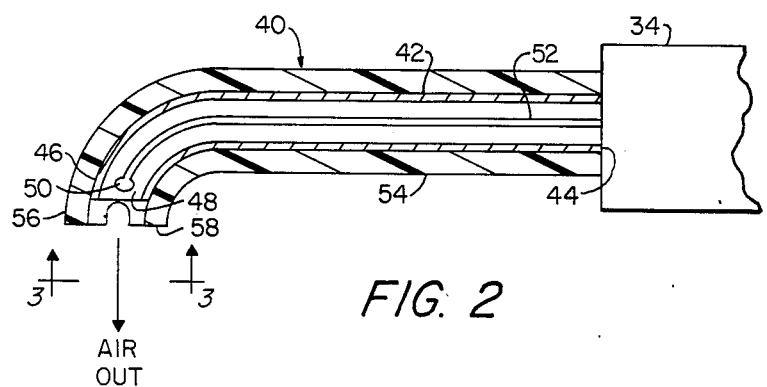
FIG. 2 is an enlarged view of the probe assembly of the FIG. 1 embodiment, partially cut-away, with a portion of the probe assembly in cross section in order to reveal the temperature sensor.

Referring to FIGS. 1 and 2, probe assembly 20 includes vortex tube 24 for cooling the incoming compressed air provided from controller 22 over supply line 26 to a temperature below or at the lower limit of the range of desired temperatures, i.e., a temperature below about 0° C. Vortex tube 24 generally includes a vortex generation chamber (not shown) having an air inlet port 28 connected to supply line 26 and adapted to provide a cold airstream into the cold air tube 30 and a hot air exhaust into the hot air exhaust tube 32. The tubes 30 and 32 are connected to the chamber in any known manner. Where vortex tube 24 is to be used for testing the sensitivity of teeth, the vortex tube is preferably of a type that is commercially available, such as the model 106 sold commercially by the Vortec Corporation of Cincinnati, Ohio. The model 106 vortex tube is specifically designed by the manufacturer to operate with compressed air supplied at a flow rate of 8 cfm at a relatively high pressure, in the order of 100 psi, so as to provide an airstream at a relatively low temperature. However, in the preferred embodiment, the apparatus is used to test the sensitivity of teeth at lower flow rates and pressures. Specifically, the air source (not shown) typically provided in a dental chair provides an airstream in the order of 1 cfm at a pressure of about 30 psi. This will result in an airstream of about ½ cfm at 30 psi into the cold tube 30 (and thus at the output of the probe assembly 20), which is adequate for providing the necessary stimuli to the teeth in the temperature ranges desired, i.e., between about 0° C. and 100° C.

The cold air tube 30 is pneumatically connected to the heater tube 34 for heating the cold airstream provided through tube 34 by the vortex tube 24 to the desired preset temperature. The heater tube, accordingly, includes a hollow passageway (not shown) for the pressurized airstream, and resistance heater elements 36 extending around the passageway of the heater tube for heating the cold airstream to the desired temperature set by the operator as it passes through the heater tube. Resistance heater elements 36 are connected to cable 38 over which electrical power is supplied to the elements by the controller.

Figure 3:
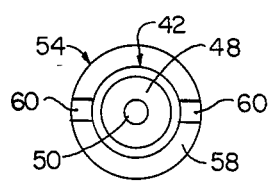
FIG. 3 is an end view of the probe assembly taken along line 3—3 in FIG. 2.

The probe assembly 20 also includes a hollow elongate probe section 40, shown generally in FIG. 1 and in greater detail in FIGS. 2 and 3. Probe section 40 includes a hollow rigid tube 42 defining a conduit for the heated airstream exiting the heater tube 34. Tube 42 has a first end 44 connected to the exit of the airstream passageway of the heater tube 34 and a curved second end 46 configured for directing the temperature controlled stream of pressurized air toward the nerve sensitive tissue. Aperture 48 is formed at the second end 46 for permitting the airstream to exit probe section 40 in a relatively controlled direction. Preferably, rigid tube 42 is made from thin-walled stainless steel tubing or other non-corrosive material having a relatively low thermal mass.

A temperature sensor 50, such as a thermocouple or thermal resistor, is disposed in the tube 42 in proximity to aperture 48. Sensor leads 52 extend through the tube 42 to the heater tube 36 where the leads are fed through the cable 38 to the controller 22 so that the sensor 50 is connected the controller control unit, described in greater detail in FIG. 4, hereinafter.

A hollow resilient sleeve 54 covers the tube 42. The sleeve grips the tube in a tight fitting manner so that it cannot unintentionally slip off. The sleeve includes the end portion 56 (FIG. 2) that extends beyond aperture 48 of the tube 42 terminating at the end surface 58 so as to protect the end of the rigid tube 42 and, in particular, the sensor 50. The end portion 56 of the sleeve 54, where the airstream exits (FIG. 3), is formed so as to permit pressurized fluid to escape when the end surface 58 (FIG. 2) of resilient sleeve 54 is placed against the surface of the nerve sensitive tissue. In particular, one or more radially extending slots 60 (two being shown in FIG. 3 in diametrically opposed positions) are formed in end surface 58 of the sleeve 54 so as to extend entirely through the wall of end portion 58 and provide an exit for the escaping airstream. Preferably, sleeve 54 is made from a suitable soft, resilient material, such as silicon rubber, so that after usage it can be easily removed from tube 42 so that the sleeve can be sterilized by known procedures, such as chemical or autoclaving techniques.

Figure 4:
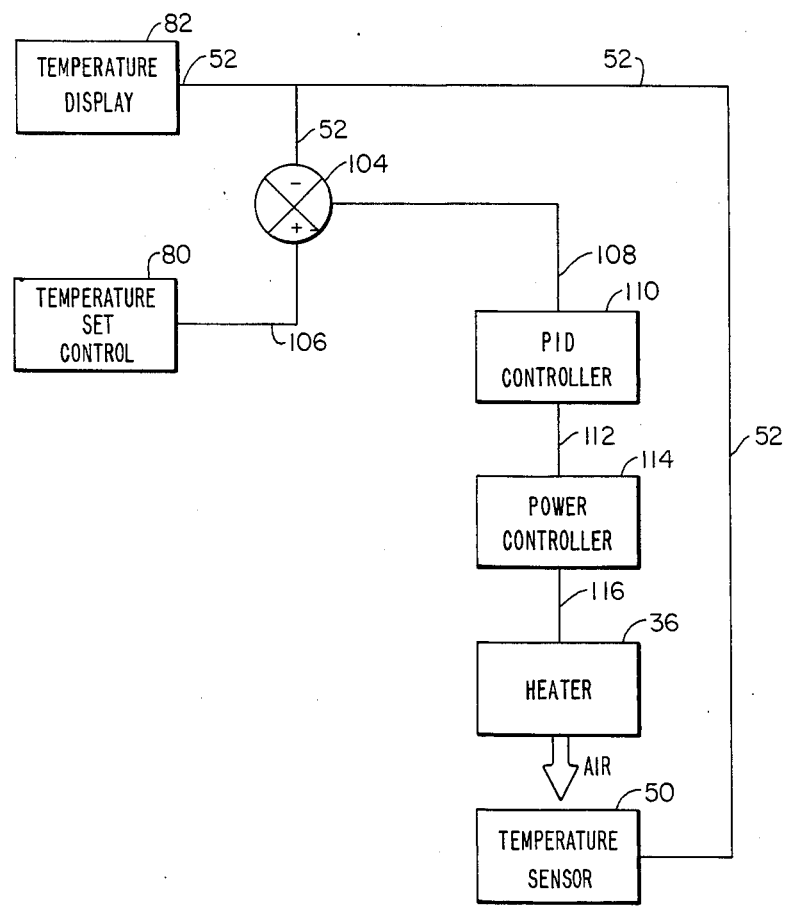
FIG. 4 is a block diagram of the the temperature controller of the FIG. 1 embodiment.

As previously described, the probe assembly 20 is controlled by temperature controller 22, best shown in FIGS. 1 and 4. Controller 22 comprises housing 76 having a front panel 78. Front panel 78 includes temperature set control 80 for setting the temperature at which the pressurized fluid will be emitted from probe assembly 20 and temperature display 82 for visually displaying the temperature of the pressurized fluid as detected by sensor 50 as the pressurized fluid passes through aperture 48 of rigid tube 42. Temperature set control 80 comprises, for example, a rotatably adjustable variable resistance device, such as a potentiometer, whose output signal varies as a function of the position of the control 80 so as to represent any preselected temperature within a range of temperatures of the airstream to be provided by the probe assembly. A keypad or an up switch and a down switch may also be satisfactorily employed as temperature set control 80. Alternatively, although not shown, for convenience, temperature set switch 80 may be mounted on probe assembly 20 and connected through cable 38 to temperature controller 22. Temperature display 82 may be either an analog or a digital display. Also mounted on front face 78 are power on/off switch 84 for selectively connecting the electrical power provided over cord 90 into the system and pressurized fluid on/off switch 86 for connecting the supply line 26 to the source line 92 connected to a source of pressurized fluid.

The interconnection of the various elements of controller 22 is indicated schematically in FIG. 4. For clarity of illustration the various elements in FIG. 4 are not shown connected to a source of power. It is to be understood, however, that power is supplied to these elements over line 90 and through switch 84, and that the power can be either AC or DC. Temperature sensor 50 is connected over line 52 to the negative input of summing junction 104 and to the input of temperature display 82. Temperature set control 80 is connected over line 106 to the positive input of summing junction 104. The signal provided to the negative input of summing junction 104 is subtracted from the signal provided to the positive input and the result is carried from the junction over line 108 to proportional, integration, and derivative ("PID") contoller 110. The use of PID controllers is well known, as described and illustrated in Dorf, R. C., *Modern Control Systems,* Reading, MA, Addison-Wesley, 1983, p. 379–383, TJ216.D67. PID controllers, also known as three-mode controllers or process controllers, are frequently connected in the forward path of a feedback control system for providing steady-state accuracy of the control system while at the same time maintaining the transient performance of the control system within acceptable limits. The PID controller may be either an analog or digital system as is well known. The output of PID controller 110 is connected over line 112 to power controller 114. The output of PID controller 110 constitutes the gate or control signal for power controller 114. The latter is connected over line 116 to heater 36. Power controller 114 may include a triac switch, a silicon control rectifier (SCR), or the like, if heater 36 is an AC heater, or a transistor if heater 36 is a DC type heater, both the triac switch, SCR and transistor being adapted to provide a level of power on line 116 as a function of the gate or control signal provided from PID controller 110 over line 112.

When the airstream temperature detected by sensor 50 is below the set temperature, indicating the airstream is too cold, the resultant signal from summing junction 104 will have a positive magnitude. This signal, after being compensated in PID controller 110, is carried over line 112 to power controller 114 causing the power controller to increase by an appropriate amount the power supplied to heater 36. This increase in power elevates the temperature of the airstream emitted from probe 40. When the airstream temperature detected by sensor 50 is greater than the temperature set at control 80, indicating the airstream is too hot, the resultant signal from summing junction 104 will have a negative magnitude. This signal after being compensated in PID controller 110 is carried over line 112 to power controller 114 causing the latter to decrease by an appropriate amount the power supplied to heater 36. This decrease in power lowers the temperature of the airstream emitted from probe 40. The system thus tends to stabilize around the temperature point where the airstream temperature sensed by sensor 50 approximately equals the temperature set by the control 80.

In operation, the system shown is connected to a source of pressurized air over line 92 and to a source of power through power line 90. If necessary, resilient sleeve 54 can be removed and replaced with an identical sleeve 56 which has been properly sterilized. Then, power switch 84 and pressurized fluid switch 86 are turned on.

As described in "A Short Course on Vortex Tubes and Application Notes", published by Vortec Corporation of Cincinnati, Ohio, 1982, the compressed air passes through inlet port 28 of the vortex tube 24 and enters the vortex generation chamber where the air is made to spin at high angular velocities. A first hollow cylindrical spinning airstream of heated air travels from the generation chamber through the length of hot air exhaust tube 32 where it is exhausted. A second cylindrical cold airstream spinning inside of the first heated airstream at the same angular velocity as, but traveling in an opposite linear direction to, the first heated airstream is exhausted from cold air tube 30.

The cooled compressed air exhausted from cold air exhaust tube 30 will be at a temperature below or at the lower limit of the range of temperatures desired, e.g. about 0° C. The cooled compressed air travels through the interiors of heat tube 34 where it is heated approximately to the desired temperature set by temperature set switch 80, between about 0° C. and 100° C. The heated airstream is passed through rigid tube 42 and is exhausted from the probe section 40. By mounting vortex tube 24 and heater tube 36 in close proximity to probe section 40 (as opposed to a position remote from the probe assembly) and, in particular, to the tissue under test, cooling and heating losses are minimized. Thus, there are no cooling losses over line 26 or supply line 92 since compressed air may be supplied to vortex tube 24 at ambient temperature. Vortex tube 24 contains no moving parts and, therefore, tends to be a reliable source of "refrigeration".

When it is desired to apply a stimulus to the tissue under test, temperature set control 80 is moved to the position indicating the desired temperature, wherein a corresponding signal is provided on line 106 to the positive input of summing junction 104. Temperature sensor 50 provides a signal to the negative input of summing junction 104 representative of the temperature of the airstream exiting the probe section 40 and sensed by the sensor. Display 82 provides the operator with an indication of the temperature of the airstream so that he or she can determine when the desired temperature is reached.

Next, probe assembly 20 is positioned by the operator so that soft rubber end surface 58 of resilient sleeve 56 contacts the surface of the tissue under test. In this position, the temperature-controlled compressed air strikes the tissue under test and exits through slots 60.

It should be appreciated that although the sensor 50 is proximate to the end surface 58 of the sleeve 54, it does not directly contact, but is spaced from, the nerve sensitive tissue under test, and therefore only a small error occurs in measuring the actual temperature of the airstream applied to the tissue under test. However, since only sleeve 56 is replaced with each patient use, the spacing of the sensor from the tissue will always be the same with the result that the small error will always be consistent, and therefore can be ignored in most applications. It may even be desirable to adjust the value displayed on display 82 to take into account this error.

Threshold thermal sensitivity levels may be determined by monitoring a patient's response to the application of increasingly hot or increasingly cold streams of compressed air through the range of temperatures. By recording the temperature level(s) of compressed air applied to a tooth at which the patient experiences pain or discomfort, data may be accumulated that is useful in monitoring changes over time of various dental conditions, which can be useful in developing new dental products, such as dentifrices.

Advantageously, the sleeve 56 can be easily removed for sterilization without disturbing the rigid tube 48 and in particular the sensor 50. The end portion 56 of the sleeve 54 extends beyond the end of the rigid tube 42 so as to provide a softer, pliable material which contacts the nerve sensitive tissue. This is advantageous because less pressure need be applied to the tissue minimizing the effects of a defacto mechanical stimulus which may interfer with the accuracy of the test.

While the dental probe of the present invention preferably uses compressed air in generating the hot and cold stimuli, other pressurized fluids, such as water may also be advantageously employed. In the event liquid pressurized fluids are used, vortex tube 24 is eliminated and the pressurized fluid is supplied directly to heat tube 34. A refrigeration system separate from probe assembly 20 for cooling the pressurized fluid before it is supplied to heat tube 34 is required.

In addition to the above-noted advantages of the present invention, it should be appreciated that by utilizing the vortex tube 24 to cool the air to a temperature below or at the lower limit of the desired range of temperatures, and a heater tube 34 to heat the cooled air to the desired temperature, the testing temperatures of the airstream can simply and easily be achieved.

The present invention is useful without modification for measuring the nerve sensitivity of other tissue, such as gums and skin, or other test objects. Sensitivity measurement of such other tissue is performed in the same manner in which sensitivity of teeth is measured.

Since certain changes may be made in the above apparatus without departing from the scope of the invention herein involved, it is intended that all matter contained in the above description or shown in the accompanying drawing shall be interpreted in an illustrative and not in a limiting sense.

What is claimed is:

1. A device for use in determining thermal sensitivity of nerve sensitive tissue to hot and cold stimuli, said device comprising:
    portable probe means for selectively directing a stream of temperature controlled, pressurized fluid into direct thermal contact with said tissue so that any heat transferred between said fluid and said tissue is transferred by forced convection; and
    temperature control means adapted to be connected to a source of said pressurized fluid and coupled to said probe means for providing said temperature controlled, pressurized fluid to said probe means, said temperature control means comprising cooling means for cooling said stream of pressurized fluid below or at the lower limit of a range of desired temperatures and means for heating the cooled stream to a preselected temperature within said range.

2. A device according to claim 1, wherein said cooling means is adapted to be connected to said source of pressurized fluid, and said heating means is disposed downstream from and in fluid communication with said cooling means so as to heat said stream of pressurized fluid cooled by said cooling means.

3. A device according to claim 2, wherein said cooling means for cooling said stream of pressurized fluid is disposed in said probe means.

4. A device according to claim 3, wherein said pressurized fluid is compressed air, and said cooling means includes a vortex tube for cooling said compressed air.

5. A device according to claim 1, wherein said temperature control means comprises temperature selector means for setting the level of said preselected temperature.

6. A device according to claim 5, wherein said probe means comprises a hollow tubular body having oppositely disposed first and second ends, said first end is constructed to receive said pressurized fluid and said second end is constructed to emit said stream of pressurized fluid to the exterior environment adjacent said second end.

7. A device according to claim 6, wherein said heating means includes a resistance heater and said temperature control means further comprises:
    flow control means secured to said housing for controlling the flow of pressurized fluid delivered by said source to said cooling means; and
    power control means for controlling the power supplied to said resistance heater so as to control the heat output of said heating means so that said stream of pressurized fluid emitted from said second end is maintained at said preselected temperature.

8. A device for use in determining thermal sensitivity of nerve sensitive tissue to hot and cold stimuli, said device comprising:
    portable probe means for selectively directing a stream of temperature controlled, compressed air in the direction of said tissue; and
    temperature control means adapted to be connected to a source of said compressed air and coupled to said probe means for providing said temperature controlled, compressed air to said probe means, said temperature control means comprising cooling means, including a vortex tube adapted to be connected to said source of compressed air and disposed in said probe means, for cooling said stream of compressed air below or at the lower limit of a range of desired temperatures, and means for heating the cooled stream to a preselected temperature within said range, wherein said heating means is disposed downstream from and in fluid communication with said cooling means so as to heat said stream of compressed air cooled by said cooling means.

9. A device according to claim 8, wherein said means for heating said cooled stream includes a resistance heater disposed in said probe means for heating cooled air emitted from said vortex tube.

10. A device for use in determining thermal sensitivity of nerve sensitive tissue to hot and cold stimuli, said device comprising:
    portable probe means for selectively directing a stream of temperature controlled, pressurized fluid in the direction of said tissue, wherein said probe means comprises a hollow tubular body having oppositely-disposed first and second ends, said first end for receiving said pressurized fluid and said second end for emitting said stream of pressurized fluid; and temperature control means, adapted to be connected to a source of said pressurized fluid and coupled to said probe means, for providing said temperature controlled, pressurized fluid to said probe means, said temperature control means comprising cooling means for cooling said stream of pressurized fluid below or at the lower limit of a range of desired temperatures and means, including a resistance heater, for heating the cooled stream to a preselected temperature within said range, and wherein said temperature control means further comprises (a) temperature selector means for setting the level of said preselected temperature, (b) a housing, (c) a flow control means secured to said housing for controlling the flow of pressurized fluid delivered by said source to said cooling means, and (d) power control means for controlling the power supplied to said resistance heater so as to control the heat output of said heating means so that said stream of pressurized fluid emitted from said second end is maintained at a substantially constant level at said preselected temperature.

11. A device according to claim 10, wherein said power control means further comprises:

sensor means disposed in the interior of said hollow tubular body for sensing the temperature of said pressurized fluid emitted from said second end;

power switch means mounted on said housing for turning on and off the power supplied to said heating means;

temperature set means mounted on said housing for selecting the level of said preselected temperature of said pressurized fluid emitted from said second end;

temperature display means for displaying the temperature of said pressurized fluid emitted from said second end; and control circuitry means for varying the flow of power to said resistance heater so as to maintain the temperature of said pressurized fluid emitted from said second end at the preselected level set by said temperature set means, said control circuitry means being connected to said sensor means, said power switch means, said temperature set means, said temperature display means and said resistance heater.

12. A device according to claim 11, wherein said cooling means comprises a vortex tube for removing heat from pressurized fluid received from said source so as to cool said pressurized fluid to a temperature below or at the lower limit of said range.

13. A device according to claim 12, wherein said vortex tube further comprises a hot air exhaust tube for removing pressurized fluid heated by said vortex tube and a cold air tube pneumatically coupled to said hollow tubular body at said first end for supplying pressurized fluid cooled by said vortex tube to said hollow tubular body.

14. A device according to claim 13, further including a resilient sleeve disposed around said tubular body, said resilient sleeve comprising an end surface positioned at the second end of said tubular body and adapted to engage the outer surface of a tooth, said sleeve including at least one slot formed in said end surface to permit a stream of said pressurized fluid to be emitted through said slot when said end surface contacts said tissue.

15. A device according to claim 14, wherein said resilient sleeve further comprises an aperture formed in said end surface to permit said pressurized fluid to be emitted from said second end, said slot extending radially through said resilient sleeve.

16. A device according to claim 14, wherein said resilient sleeve is selectively removable from said tubular body.

17. A device according to claim 16, wherein said sleeve is made from silicon rubber.

18. A device according to claim 14, wherein said tubular body and sleeve are curved adjacent said second end of said tubular body so as to facilitate placement of said end surface of said sleeve on the surface of a tooth.

19. A device for emitting a temperature controlled stream of pressurized fluid, said device comprising:

portable probe assembly means, adapted to be connected to a source of pressurized fluid, for emitting a stream of said pressurized fluid, said probe assembly means including (a) cooling means, pneumatically coupled in said probe assembly means, for cooling said stream of pressurized fluid before it is emitted from said probe assembly means, (b) heating means, pneumatically coupled in said probe assembly means, for heating said stream of pressurized fluid emitted by said cooling means before it is emitted from said probe assembly means, (c) a hollow rigid probe assembly tip for emitting said stream of pressurized fluid from said device, and (d) a resilient sleeve disposed on said probe assembly tip, said resilient sleeve including an aperture for emitting said stream from said probe assembly tip; and temperature control means coupled to said heating means for controlling the heat output of said heating means so that the temperature of said stream of pressurized fluid emitted from said probe assembly means may be varied over a preselected range of levels, said temperature control means comprising temperature set means for selecting the temperature level within said range.

20. A device according to claim 19, said temperature controller means comprises:

sensor means disposed in the interior of said probe assembly tip for sensing the temperature of said stream of pressurized fluid emitted from said probe assembly tip;

power switch means for controlling the power supplied to said heating means;

temperature display means for displaying the temperature of said stream of pressurized fluid emitted from said probe assembly tip;

control circuitry means for varying the flow of power to said heating means so as to maintain the temperature of said stream of pressurized fluid emitted from said probe assembly tip at the level selected at said temperature set means, said control circuitry means being connected to said temperature set means, said sensor means, said power switch means, said temperature display means and said heating means, said control circuitry means being adapted for connection to a source of power.

21. A method of measuring the thermal sensitivity of nerve sensitive tissue at each of a plurality of test temperatures within a range of temperatures, said method comprising the steps of:

cooling a stream of fluid below or at the lower limit of the range of temperatures;

heating the cooled stream of fluid to any one of the temperatures of the plurality in response to a control signal;

emitting said fluid stream from a tip of a probe;

positioning said tip relative to the surface of nerve sensitive tissue of a patient so that the stream emitted from said tip contacts said surface; and generating the control signal, wherein said step of generating said control signal includes the steps of (1) setting the temperature of said stream to a selected level of one of said test temperatures, (2) measuring the temperature of said stream as it is emitted from said tip, and (3) adjusting said control signal so as to vary the heat applied to said stream until the temperature of said stream reaches said selected level.

22. A method according to claim 21, wherein said step of cooling said stream of fluid includes the step of passing said stream through a vortex tube.

23. A method according to claim 21, wherein said step of generating said control signal further includes the step of readjusting said control signal so as to vary the heat applied to said stream after said tip is positioned relative to said surface of nerve sensitive tissue.

24. A method according to claim 21, wherein said step of positioning said tip includes the step of engaging said tip with the surface of said nerve sensitive tissue.

25. A device for emitting a temperature controlled stream of pressurized fluid comprising:

portable probe assembly means, adapted to be connected to a source of pressurized fluid, for emitting a stream of said pressurized fluid into the exterior environment adjacent said probe means, said probe assembly means including (a) cooling means pneumatically coupled in said probe assembly means for cooling said stream of pressurized fluid before it is emitted from said probe assembly means and (b) heating means pneumatically coupled in said probe assembly means for heating said stream of pressurized fluid emitted by said cooling means before it is emitted from said probe assembly means; and temperature controller means coupled to said heating means for controlling the heat output of said heating means so that the temperature of said stream of pressurized fluid emitted from said probe assembly means may be varied over a preselected range of levels, said temperature controller means comprising temperature set means for selecting the temperature level within said range.

26. A device according to claim 25, wherein said probe assembly means comprises a hollow rigid probe assembly tip for emitting said stream of pressurized fluid from said device, and a resilient sleeve disposed on said probe assembly tip, said resilient sleeve including an aperture for emitting said stream from said probe assembly tip.

* * * * *